United States Patent [19]

Brown

[11] Patent Number: 5,069,551

[45] Date of Patent: Dec. 3, 1991

[54] METHOD AND APPARATUS OF MEASURING UNBURNED CARBON IN FLY ASH

[75] Inventor: Robert C. Brown, Ames, Iowa

[73] Assignee: Iowa State University Research Foundation, Inc., Ames, Iowa

[21] Appl. No.: 440,686

[22] Filed: Nov. 24, 1989

[51] Int. Cl.[5] ...................... G01N 21/85; G01N 15/02
[52] U.S. Cl. .................................... 356/432; 356/335
[58] Field of Search ............... 356/440, 432, 246, 436, 356/438, 432 T, 335, 73; 250/345

[56] References Cited

U.S. PATENT DOCUMENTS

| HB,572 | 2/1989 | Hansen ................................ 356/439 |
| 3,614,230 | 10/1971 | Crawford ............................ 356/36 |
| 4,303,343 | 12/1981 | Patel et al. ......................... 356/432 |
| 4,436,428 | 3/1984 | Watanabe et al. ................. 356/432 |
| 4,516,858 | 5/1985 | Gelbwachs ......................... 356/437 |
| 4,622,845 | 11/1986 | Ryan et al. .............................. 73/24 |
| 4,722,602 | 2/1988 | Kitamori et al. ................... 356/336 |
| 4,740,086 | 4/1988 | Oehler et al. ...................... 356/432 |
| 4,808,828 | 2/1989 | Kitamori et al. ................. 250/458.1 |

OTHER PUBLICATIONS

In-Situ Measurements of Aerosol Absorption with a Resonant Cw Laser Spectrophone—C. W. Bruce & R. G. Pinnick—Applied Optic 2, vol. 16, No. 7, Jul. 1977.
Japar, Steven M. and Szkarlat, Ann Cuneo, *Combustion Science and Technology*, 1981, vol. 24, pp. 215-219, "Measurement of Diesel Vehicle Exhaust Particulate Using Photoacoustic Spectroscopy".

*Primary Examiner*—Vincent P. McGraw
*Assistant Examiner*—LaCharles P. Keesee, II
*Attorney, Agent, or Firm*—Zarley, McKee, Thomte, Voorhees & Sease

[57] ABSTRACT

A method and apparatus are shown to measure unburned carbon particles in the exhaust of a combustor. Photoacoustic absorption spectrometry is employed to measure the presence of the unburned carbon. Especially helpful in these measurements is a vertically elongated photoacoustic cell in which high flow velocities are maintained to prevent particles from settling. These measurements are useful in determining the efficiency of coal-fired combustors.

7 Claims, 2 Drawing Sheets

○ DATA POINTS
--- CELL NOISE

METHOD AND APPARATUS OF MEASURING UNBURNED CARBON IN FLY ASH

BACKGROUND OF THE INVENTION

In combustors which use coal as fuel, at times there will be a loss of efficiency in burning the coal which results in unburned carbon particles being emitted in the exhaust. The exhaust from such a combustor will contain fine solid particles of ashes, dust, and carbonaceous material carried out from the burning fuel by the exhaust draft, and is referred to in the field as fly ash. The presence of unburned carbon particles in fly ash is an indicator that there is a loss of efficiency in the system. Detecting such particles is important in calculating the combustion efficiency in coal-fired combustors such as boilers.

Present methods which are used in measuring unburned carbon particles in fly ash are tedious and time consuming. Carbon which is emitted from combustors can be classified as either grit or soot. Grit is defined as the material which is retained on a 200-mesh USA sieve and represents unburned char. Soot is composed of submicron particles less than 0.1 μm in diameter, is formed by gas phase processes. The mass of soot which leaves a combustor is too small to effect combustion efficiency. Currently, unburned carbon in fly ash is measured by sampling flue gas from the exhaust of a combustor and using a particulate filter to remove fly ash from the flue. The fly ash is then dried and weighed before being placed in a furnace for several hours in order to burn off the carbon. The fly ash is then reweighed to find the percent of carbon. This can involve several hours and rarely yields a large enough sample through filtering to investigate a transient phenomenon in the combustor. The accuracy of the technique is also limited by problems associated with isokinetic sampling and filtration techniques.

This invention relates to an improved method of measuring the unburned carbon content in fly ash. It involves the application of photoacoustic absorption spectroscopy as a method for on-line monitoring of unburned carbon in fly ash. Photoacoustic absorption spectroscopy (PAS) is based on the periodic heating of a gas when amplitude-modulated radiation is absorbed by the gas or by particles suspended in the gas. This technique has been used, for example, to measure mass concentrations of soot in the exhaust of diesel engines, such as that discussed in Japar, S. M., Moore, J., and Killinger, D. K., "The Use of Photoacoustic Spectroscopy to Characterize and Monitor Soot in Combustion Processes.", *Combustion Science Technology*, Vol. 24, pp. 215-219 (1981). However, this process has not been applied to particles as large as unburned carbon in fly ash. Instead, it is applied towards soot and similar material which has a diameter of about 0.1 microns or less.

Two important features of PAS make it especially suitable for detection of carbon in flue gas. The first of these is the technique's ability to detect very weak absorptions. Secondly, the PAS signal is unaffected by light scattering in a particulate-laden gas flow. Instead, the acoustical signal arises only from light absorption.

Thus, it is a primary object of this invention to provide for an improved method and apparatus of measuring the unburned carbon content of exhaust from coal-fired combustors.

A further object of the invention is to provide for a method of detecting unburned carbon in combustion exhaust which employs photoacoustic absorption spectroscopy.

Yet another object of the invention is to provide for a sensitive method and apparatus of measuring unburned carbon content in combustion exhaust.

A still further object of the invention is to provide for a method of measuring unburned carbon content in combustor exhaust using photoacoustic absorption spectroscopy in which the signal is unaffected by light scattering in a particulate-laden gas flow.

Yet another object of the invention is to provide for an accurate and time efficient method and apparatus of measuring unburned carbon content in combustor exhaust.

Further objects of the invention will become apparent with the following disclosure.

SUMMARY OF THE INVENTION

The invention relates to a method and an apparatus to be used in measuring unburned carbon content in exhaust of combustors. It employs photoacoustic absorption spectroscopy in order to detect the presence of such unburned carbon, which is generally of a diameter of about 10 microns or more. It also employs a photoacoustic cell for such measurements which is vertically elongated.

DETAILED DESCRIPTION OF THE DRAWINGS

DETAILED DESCRIPTION OF THE INVENTION

Photoacoustic spectroscopy has been used to analyze particles in a medium and this process is well known in the art. E.g. Japar, supra. Basically, an excitation beam in which the amplitude is modulated is directed onto the particles to be analyzed. Absorption of light causes the particles to be periodically heated. This periodic heating produces an acoustic wave in the surrounding gas medium which is measured by a microphone placed within the apparatus. Amplitude of the PAS signal is proportional to the concentration of the particles.

Figure 1:
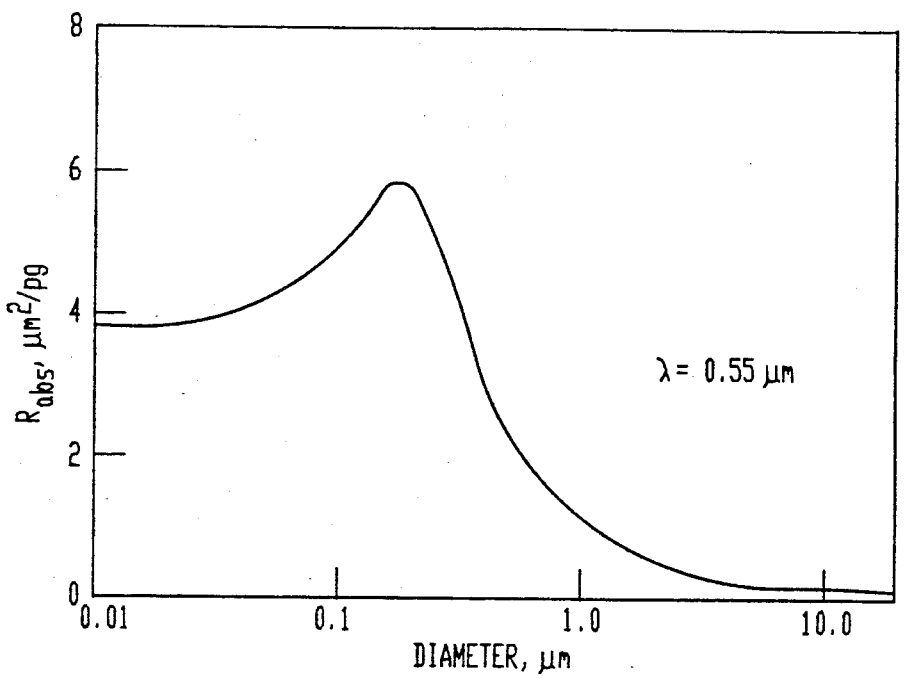
FIG. 1 is a graph which depicts absorption coefficient for carbon particles.

In the measurement of particulate mass loadings, one can define optical properties on a mass basis. Assuming that the refractive index of carbon is $m = 1.95 - 0.66i$ a plot of absorption cross section per unit mass as a function of carbon particle diameter may be plotted. This is shown in FIG. 1 for an incident wave length $\lambda$ of 0.55 μm. Soot has a diameter of about 0.1 microns in size or less. The unburned carbon, also called "char" to which the method is applied here is pure carbon and is in diameter about 10 μm to 100 μm. As FIG. 1 demonstrates, the absorption coefficient for the carbon particles is constant where the diameter is less than 0.1 μm. It is not constant for values greater than this. However, in the range of particle sizes typical for unburned carbon in fly ash, the absorption coefficient is only weakly dependent on particle size.

In other words, particle size of carbon from a combustor is large enough that the signal is not a strong function of size. Rather, measurement of total carbon emitted can be determined directly from the signal. Thus, what is measured here is not the specific particle size, but the total amount of carbon.

In employing photoacoustic absorption spectroscopy, it is necessary to calibrate the device which is used to measure the acoustic signal in order to obtain an accurate reading. A variety of calibration methods are available. For low light absorption, the PAS signal response is given by the following equation:

$$S = RP_o\gamma ML$$

Where R is the cell response (dependent upon cell geometry and light modulation frequency), $\gamma$ is the integrated mass-specific absorption coefficient for unburned carbon particles, $P_o$ is the incident power, M is the mass concentration of carbon particles, and L is the length of the cell. Cell responsivity, R, is related to cell geometry, modulation frequency, and the density and specific heat of the gaseous medium used for calibration.

Another method of calibration may be used in which a known substance is placed into the measuring device, and then the signal calibrated by adjusting it to the known acoustic signal of the substance.

The size of particles emitted from a particular combustor will not change greatly as operating conditions are changed. The device is calibrated once, then the calibration curve is used to relate signal to carbon loading. The total amount of carbon present is a measure of combustion efficiency.

Figure 2:
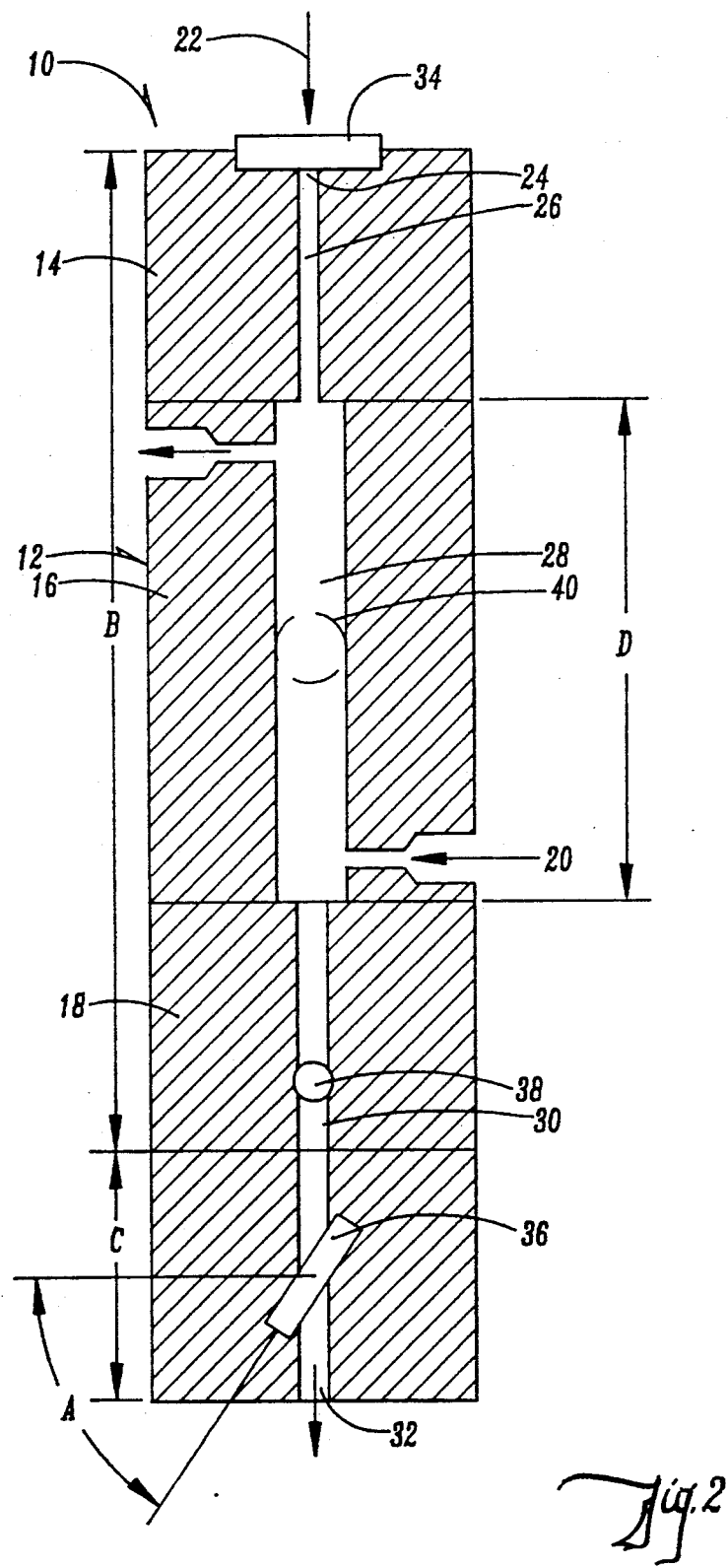
FIG. 2 is a side cross sectional view of one embodiment of a photoacoustic cell of this invention.

One embodiment of the photoacoustic cell is shown in FIG. 2. Photoacoustic cells, such as a cell generally represented at 10, are usually constructed for horizontal flow of gas through the cell. However, gravitational settling of fly ash particles within a horizontal cell would be unacceptable even for very high gas flow rates through short cells. Therefore, this cell 10 has been especially constructed for measuring photoacoustic signals generated by large particles suspended in dusty gas flows by providing that the cell 10 is vertically elongated.

In FIG. 2, the elongated cell is constructed from solid metal as in block 12. This block 12 includes an upper portion 14, a central portion 16 and a lower portion 18. The particle-laden gas flows through an inlet 20 machined in the central portion 16 of block 12. This inlet in one preferred embodiment is 1.3 cm in diameter. The excitation beam, which is often a laser, is directed so that the beam path 22 enters through a hole 24 in upper chamber 26 within upper portion 14 of block 12. Upper chamber 26 continues down to central chamber 28 which is in central portion 16 of block 12. The beam exits through a lower chamber 30 similar to the upper chamber 26 but slightly larger in diameter. Lower chamber 30 leads to exit hole 32. This embodiment allows for a window 34 over the entrance hole 24 and a second window 36 located within lower chamber 30 near exit hole 32. These windows are isolated from the gas flow in this manner to prevent particles from hitting and soiling the windows. The cell windows are made of high quality optical glass to minimize absorption in the windows, which generates background acoustical noise. The beam exits through the lower window, which is set at an angle of 56° as shown at angle A, referred to in the art as a "Brewster Angle". The Brewster Angle is a function of the wavelength of laser light. In these experiments with a HeNe laser (wavelength of 632.8 nm), the appropriate Brewster angle is 56°. This arrangement reduces reflection of light back into the cell where it would be absorbed by the walls and create acoustical noise. Upper chamber 26 is about 4 mm in diameter, central chamber 13 mm in diameter, whereas lower chamber 30 is about 5 mm in diameter in this embodiment of the invention.

Further, in this embodiment, the distance represented at line B from the top of block 12 to half way into lower block 18 is 200 mm. The remaining length of the lower portion 18 of block 12 shown at line C is 50 mm. The vertical length of central portion 16 of block 12, as shown at line D is about 102 mm. Width of the block would be about 64 mm.

It is important to note these dimensions are not critical and are given by way of example only of one embodiment of the invention.

Because of the large particles which are being analyzed with this process, it is necessary to maintain a high flow velocity of the particulate matter. This embodiment adapts a vertical flow configuration with upward flow velocities slightly higher than the terminal velocity for the largest particles expected in the gas flows. This configuration allows retaining the long cell length and operating at a relatively low flow velocity. Therefore, it is helpful if the flow velocity is high enough to prevent the particles from settling out, while low enough that it does not cause acoustical noise within the cell. The preferred velocity is within the range of 0.15 m/s up to 0.4 m/s. Yet another precaution may be taken in order to encourage the particles from settling to the bottom. This includes providing for a small flow of air into the passage that transmits the light beam to the lower window. This purge gas flow inlet shown at 38 prevents particles from reaching the lower window.

Multiple scattering of light is avoided in the photoacoustic cell by assuring that mass loadings are less than 130 $g/m^3$. Particulate emissions from pulverized coal combustors are well below this number, thus dilution of the gas flow before the photoacoustic cell will rarely be necessary.

The microphone 40 is recessed into the cell wall about half way up the cell as shown in FIG. 2. A high quality microphone that can detect low level sounds is needed in this invention. In one embodiment tested by the inventors, a General Radio model 1933 precision sound-level meter and analyzer was employed. This half-inch electret condenser microphone has a sensitivity of $-43$ dB referred to 1 V/Pa. Acoustic isolation is achieved by mounting the cell in a metal enclosure that is packed with acoustic shielding material.

A variety of modulated optical radiation sources and electronic signal processing equipment can be used to generate and detect photoacoustic signals in the cell. One embodiment employed by the inventor uses a variable-speed mechanical chopper to modulate the light beam from a 35-mW HeNe laser. Acoustic signals were processed by a narrow band prefilter to reject background noise. The signal was then processed by a lock-in amplifier and displayed and stored on a microcomputer using a digital oscilloscope periphery. The cell response, R, as a function of light modulation frequency, was determined by calibration with 462 ppm of $NO_2$ in nitrogen gas. The absorption coefficient at 632.8 nm for this concentration of $NO_2$ is estimated to be $0.0162 \pm 0.0026$ $m^{-1}$ from Hsu, D., Monts, D. and Zare, R., "Spectra Atlas of Nitrogen Dioxide 5530 to 6480 A", *Academic Press*, (New York 1978).

To generate the experimental data presented in this disclosure, a particulate supply system was used similar to a device described by Altenkirch, R. A., Peck, R. E. and Chem, S. L., "Fluidized Bed Feeding of Pulvarized Coal", *Powder Technology*, Vol. 20, pp. 189-196 (1978). This was used to generate fly ash to be measured and is not part of this invention. Particulate-laden flows were generated with a 3.8-cm-diameter fluidized bed of fly ash mixed with unburned carbon. "Synthetic" fly ash samples of variable carbon content were prepared by mixing small quantities of Illinois No. 5 coal screened to 45 μm×53 μm with fly ash from a pulverized coal boiler that has been previously heated in an oxidizing environment to remove all carbon. Particles suspended in the bed were extracted through a small orifice in the side of the bed and diluted with additional air before flowing to the photoacoustic cell. Simultaneous adjustment of fluidization and dilution air flows was used to set the desired particulate loading of the gas flow entering the photoacoustic cell.

Figure 3:
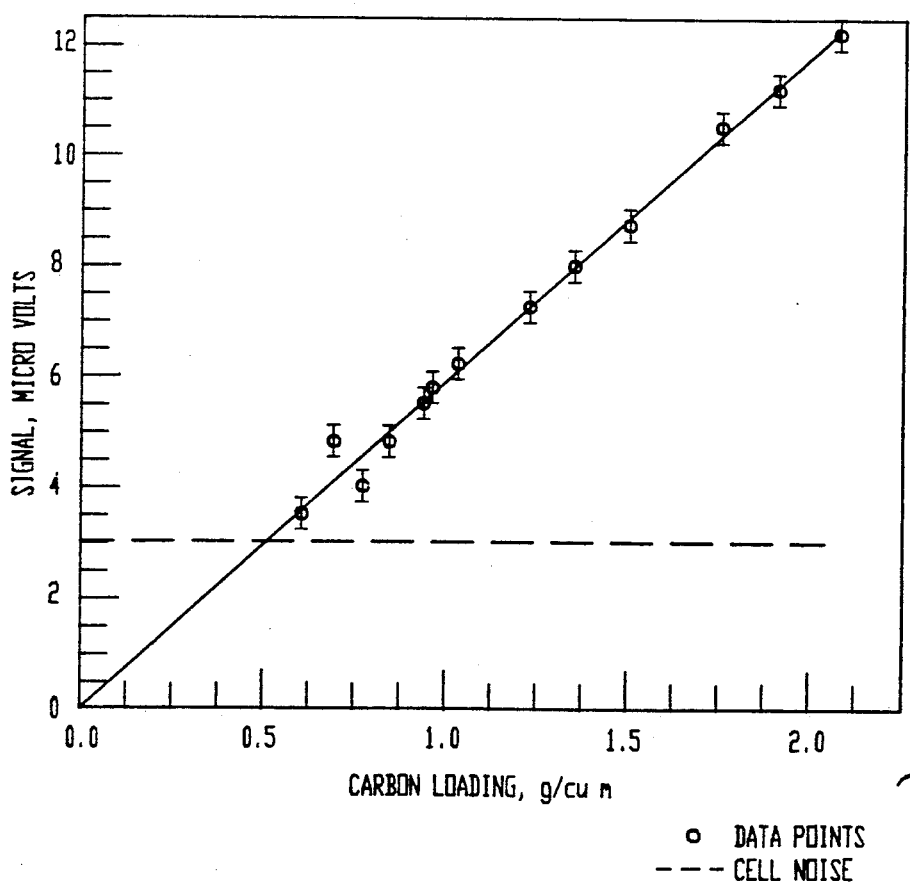
FIG. 3 is a graph showing photoacoustic signal plotted against carbon loading.

The results for total fly ash mass loading held constant and percent carbon in fly ash varied between 0 and 100% are depicted in the graph in FIG. 3 which shows the photoacoustic signal on the vertical line versus the carbon loading on the horizontal line. A linear regression analysis of these data shows a slope of 6.0 μm V-m$^3$/g and an intercept of −0.043 μmV (that is, nearly zero) with a correlation coefficient of 0.992. These results indicate that the signal is unaffected by mineral matter and is linearly proportional to the mass of carbon in the gas flow.

The foregoing is presented as a method of illustrating the invention, and is not intended to limit its scope, which will be apparent to those skilled in the art.

Thus, it can be seen that the invention accomplishes at least all of its objectives.

I claim:

1. A method for detecting loading of unburned carbon particles in the exhaust of coal-fired combustors using photoacoustic absorption spectroscopy to detect said unburned carbon, said method comprising:
    generating an excitation beam;
    directing said beam at said exhaust;
    generating photoacoustic signals by heat given off said particles in said exhaust when said beam contacts said particles;
    said signal detecting unburned carbon particles about 10 microns in diameter or larger;
    detecting photoacoustic signals generated; and
    determining carbon loading as a function of said signal.

2. A method for detecting loading of unburned carbon particles in the exhaust of coal-fired combustors using photoacoustic absorption spectroscopy to detect said unburned carbon, said method comprising:
    generating an excitation beam within a vertically elongated photoacoustic cell;
    directing said beam at said exhaust;
    said exhaust maintained at a fluctuation velocity in said cell at about 0.15 meters per second to about 0.4 meters per second;
    generating photoacoustic signals by heat given off said particles in said exhaust when said beam contacts said particles;
    detecting photoacoustic signals generated; and
    determining carbon loading as a function of said signal.

3. The method of claim 2 wherein an opening is provided into said photoacoustic cell to introduce gas to prevent said unburned carbon particles in said exhaust from settling within said cell.

4. An improvement in a photoacoustic cell to measure photoacoustic absorption spectroscopy, said improvement comprising:
    a vertically elongated cell for measuring unburned carbon particles in exhaust of coal-fired combustors; and
    means to maintain said exhaust of said combustors entering said cell at a velocity of about 0.15 meters per second to about 0.4 meters per second.

5. The cell of claim 4 wherein an opening is provided in said cell and means to allow entrance of a gas through said opening to prevent settling of said unburned carbon particles from said exhaust.

6. The cell of claim 4 further comprising a means to determine mass loading of said unburned carbon particles as a function of the acoustic signal produced by said unburned carbon particles in said cell.

7. A method for detecting loading of unburned carbon particles greater than 0.1 microns in diameter in the exhaust of coal-fired combustors using photoacoustic absorption spectroscopy to detect said unburned carbon, said method comprising:
    generating an excitation beam;
    directing said beam at said exhaust;
    generating photoacoustic signals by heat given off said particles in said exhaust when said beam contacts said particles said photoacoustic signals being calibrated to provide standard measurement;
    said signal detecting unburned carbon particles greater than 0.1 microns in diameter;
    detecting photoacoustic signals generated; and,
    comparing said signal to said standard measurements; and
    to determine carbon loading as a function of said signal.

* * * * *

UNITED STATES PATENT AND TRADEMARK OFFICE
CERTIFICATE OF CORRECTION

PATENT NO. : 5,069,551
DATED : December 3, 1991
INVENTOR(S) : Robert C. Brown

It is certified that error appears in the above-indentified patent and that said Letters Patent is hereby corrected as shown below:

In column 1, before the "BACKGROUND OF THE INVENTION" insert the following:

--Work for this invention was funded in part by a grant from the United States Department of Energy, grant nummber W-7405-ENG-82. The Government may have certain rights in this invention.--.

Signed and Sealed this

Twenty-eight Day of March, 1995

Attest:

BRUCE LEHMAN

*Attesting Officer*  *Commissioner of Patents and Trademarks*